United States Patent [19]

Richter et al.

[11] 3,976,471

[45] Aug. 24, 1976

[54] N-(ALKYLIDENEAMINOOXYMETHYL)-ALPHA-HALOACETANILIDES

[75] Inventors: Sidney B. Richter, Chicago; Chin Ching Wu, Libertyville, both of Ill.

[73] Assignee: Velsicol Chemical Corporation, Chicago, Ill.

[22] Filed: Aug. 13, 1975

[21] Appl. No.: 604,399

[52] U.S. Cl. .................................... 71/105; 71/98; 71/118; 260/558 P; 260/562 B; 260/562 R
[51] Int. Cl.² ............................................. A01N 9/20
[58] Field of Search ...... 260/562 B, 566 AE, 558 P, 260/562 R; 71/118

[56] References Cited
UNITED STATES PATENTS

| | | | |
|---|---|---|---|
| 3,268,584 | 8/1966 | Olin | 260/562 B |
| 3,547,620 | 12/1970 | Olin | 71/118 |
| 3,637,847 | 1/1972 | Olin | 260/562 B |
| 3,766,270 | 10/1973 | Hiller et al. | 71/118 X |
| 3,830,841 | 8/1974 | Ratts | 260/562 B |
| 3,903,162 | 9/1975 | Chupp | 260/562 B |

*Primary Examiner*—Helen M. S. Sneed
*Attorney, Agent, or Firm*—Robert J. Schwarz; Dietmar H. Olesch

[57] ABSTRACT

This invention discloses new compounds of the general formula

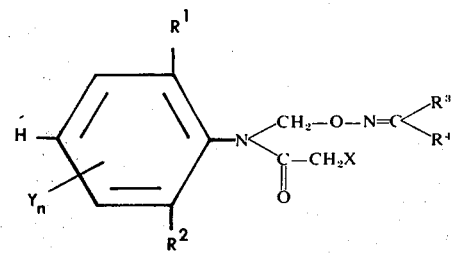

wherein $R^1$ and $R^2$ are each alkyl; Y is selected from the group consisting of hydrogen, alkyl, alkoxy, halogen, cyano, alkylthio, haloalkyl, alkoxyalkyl and alkylthioalkyl; n is an interger from 0 to 2; $R^3$ and $R^4$ are each selected from the group consisting of hydrogen and alkyl, or $R^3$ and $R^4$ together can form a cycloalkyl group of from 3 to 7 carbon atoms; and X is chlorine or bromine. The compounds of the foregoing description are useful as herbicides.

10 Claims, No Drawings

N-(ALKYLIDENEAMINOOXYMETHYL)-ALPHA-HALOACETANILIDES

This invention relates to new compositions of matter and more specifically relates to new chemical compounds of the formula

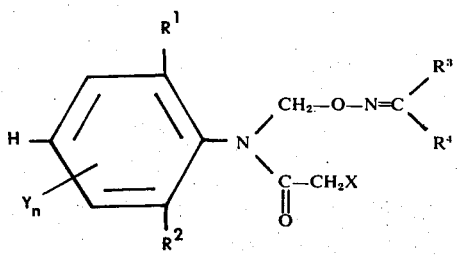

wherein $R^1$ and $R^2$ are each alkyl; Y is selected from the group consisting of hydrogen, alkyl, alkoxy, halogen, cyano, alkylthio, haloalkyl, alkoxyalkyl and alkylthioalkyl; n is an integer from 0 to 2; $R^3$ and $R^4$ are each selected from the group consisting of hydrogen and alkyl, or $R^3$ and $R^4$ together can form a cycloalkyl group of from 3 to 7 carbon atoms; and X is chlorine or bromine.

The compounds of the present invention are unexpectedly useful as herbicides.

In a preferred embodiment of the present invention $R^1$ and $R^2$ are each lower alkyl; Y is selected from the group consisting of hydrogen, lower alkyl, lower alkoxy, chlorine, bromine, fluorine, cyano, lower alkylthio, lower chloroalkyl, lower bromoalkyl, trifluoromethyl, lower alkoxy(lower)alkyl and lower alkylthio(lower)alkyl; n is an integer from 0 to 2; $R^3$ and $R^4$ are each selected from the group consisting of hydrogen and lower alkyl, or $R^3$ and $R^4$ together form a cycloalkyl group of from 3 to 7 carbon atoms; and X is chlorine or bromine.

The term "lower" as used herein designates a straight or branched carbon chain of up to six carbon atoms.

The compounds of the present invention can be readily prepared by reacting a compound of the formula

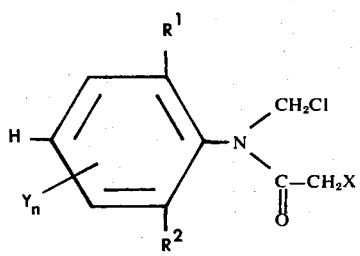

wherein Y, $R^1$, $R^2$, X and n are as heretofore described, with a compound of the formula

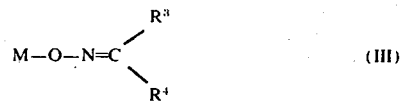

wherein $R^3$ and $R^4$ are as heretofore described, and M is sodium or potassium. This reaction can be effected by combining the compounds of formulae II and III, each dissolved in a suitable inert organic solvent, such as methanol, at room temperature with stirring. After a period of about one hour the reaction mixture can be filtered to remove sodium or potassium chloride which form as a precipitate. The filtrate can then be washed with water, or first stripped of solvent if a water-miscible solvent such as methanol was used, and then redissolved in a water-immiscible solvent such as ethyl acetate, followed by water washing. The washed solution can then be dried and stripped of solvent to yield the desired product. This product can be used as such or can be further purified by conventional techniques well known in the art.

The compounds of formula II are known in the art, and their preparation is described in U.S. Pat. No. 3,637,847.

The compounds of formula III, when not readily available, can be conveniently prepared from the corresponding oxime by reaction with alcoholic sodium or potassium hydroxide. The reaction can be readily effected in ethanol by stirring the reactants at room temperature. The desired product can then be recovered upon evaporation of the solvents used and can be used as such or further purified by washing, triturating or the like.

The manner in which the compounds of the present invention can be prepared is more specifically illustrated in the following examples.

EXAMPLE 1

Preparation of N-Methylene-2,6-diethylaniline 2,6-Diethylaniline (149.2 grams; 1.0 mole), paraformaldehyde (40 grams), a 25% solution of trimethylamine (1.7 grams) and heptane were charged into a glass reaction vessel equipped with a mechanical stirrer, thermometer and reflux condenser connected to a Dean-Stark trap. The reaction mixture was heated and the water formed removed by azeotropic distillation. When no more water could be removed, the reaction mixture was stripped of solvent and distilled to yield the desired product N-methylene-2,6-diethylaniline as a colorless oil having a boiling point of 65°C.

EXAMPLE 2

Preparation of N-Chloromethyl-2,6-diethyl-α-chloroacetanilide

N-Methylene-2,6-diethylaniline (107.7 grams; 0.66 mole) was charged into a glass reaction vessel equipped with a mechanical stirrer, thermometer, reflux condenser and addition funnel. Chloroacetyl chloride (75.3 grams; 0.66 mole) was then added dropwise to the reaction vessel with stirring and cooling. After the addition was completed, the reaction mixture was heated at reflux for a period of about 5 minutes. After this time the reaction mixture was cooled to room temperature, was washed with water and was dried over anhydrous sodium sulfate to yield the desired product N-chloromethyl-2,6-diethyl-α-chloroacetanilide as a brown oil.

EXAMPLE 3

Preparation of the Sodium Salt of Cyclopentanone Oxime

Cyclopentanone oxime (9.9 grams; 0.1 mole) dissolved in ethanol (50 ml) and a solution of sodium hydroxide (4.4 grams; 0.11 mole) in ethanol (50 ml) were charged into a glass reaction vessel and were stirred for a period of about 30 minutes. After this time the reaction mixture was stripped of solvent, and the residue was triturated in benzene. The benzene layer was then decanted to yield as the residue the desired product the sodium salt of cyclopentanone oxime as pale brown flakes.

EXAMPLE 4

Preparation of N-(Cyclopentylideneaminooxymethyl)-2,6-diethyl-α-chloroacetanilide N-Chloromethyl-2,6-diethyl-α-chloroacetanilide (2.74 grams; 0.01 mole) dissolved in ethanol (10 ml) and the sodium salt of cyclopentanone oxime (1.33 grams; 0.01 mole) dissolved in ethanol (10 ml) were charged into a glass reaction vessel and stirred at room temperature for a period of about 1 hour. After this time the reaction mixture was filtered to remove the sodium chloride formed. The filtrate was then stripped of solvent and the residue dissolved in ethyl acetate. The resulting solution was washed with water, dried over anhydrous sodium sulfate and stripped of solvent to yield an oil. The oil was filtered to yield the desired product N-(cyclopentylideneaminooxymethyl)-2,6-diethyl-α-chloroacetanilide as a brown oil having a refractive index of 1.533 at 27°C.

EXAMPLE 5

Preparation of the Sodium Salt of Cyclobutanone Oxime

Cyclobutanone oxime (0.10 mole) dissolved in ethanol (50 ml) and a solution of sodium hydroxide (0.11 mole) in ethanol (40 ml) are charged into a glass reaction vessel and are stirred for a period of about 30 minutes. After this time the reaction mixture is stripped of solvent and the residue is triturated in benzene. The benzene is then decanted to yield as the residue the desired product the sodium salt of cyclobutanone oxime.

EXAMPLE 6

Preparation of N-(Cyclobutylideneaminooxymethyl)-2,6-dimethyl-α-chloroacetanilide N-Chloromethyl-2,6-dimethyl-α-chloroacetanilide (0.05 mole) dissolved in ethanol (150 ml) and the sodium salt of cyclobutanone oxime (0.05 mole) dissolved in ethanol (100 ml) are charged into a glass reaction vessel and stirred at room temperature for a period of about 1 hour. After this time the reaction mixture is filtered to remove the sodium chloride formed. The filtrate is then stripped of ethanol and the residue is dissolved in ethyl acetate. The resulting solution is washed with water, is dried over anhydrous magnesium sulfate and filtered. The filtrate is then stripped of solvent to yield the desired product N-(cyclobutylideneaminooxymethyl)-2,6-dimethyl-α-chloroacetanilide as the residue.

EXAMPLE 7

Preparation of the Sodium Salt of 2-Butanone Oxime

2-Butanone oxime (0.10 mole) dissolved in ethanol (50 ml) and a solution of sodium hydroxide (0.11 mole) in ethanol (40 ml) are charged into a glass reaction vessel and are stirred for a period of about 30 minutes. After this time the reaction mixture is stripped of solvent, and the residue is triturated in benzene. The benzene is then decanted to yield as the residue the desired product the sodium salt of 2-Butanone oxime.

EXAMPLE 8

Preparation of N-(1-Methylpropylideneaminooxymethyl)-2,6-dipropyl-α-chloroacetanilide N-Chloromethyl-2,6-dipropyl-α-chloroacetanilide (0.05 mole) dissolved in ethanol (150 ml) and the sodium salt of 2-butanone oxime (0.05 mole) dissolved in ethanol (100 ml) are charged into a glass reaction vessel and stirred at room temperature for a period of about 1 hour. After this time the reaction mixture is filtered to remove the sodium chloride formed. The filtrate is then stripped of ethanol, and the residue is dissolved in ethyl acetate. The resulting solution is washed with water, is dried over anhydrous magnesium sulfate and filtered. The filtrate is then stripped of solvent to yield the desired product N-(1-methylpropylideneaminooxymethyl)-2,6-dipropyl-α-chloroacetanilide as the residue.

EXAMPLE 9

Preparation of the Potassium Salt of Cyclohexanone Oxime

Cyclohexanone oxime (0.10 mole) dissolved in ethanol (50 ml) and a solution of potassium hydroxide (0.11 mole) in ethanol (40 ml) are charged into a glass reaction vessel and are stirred for a period of about 30 minutes. After this time the reaction mixture is stripped of solvent, and the residue is triturated in benzene. The benzene is then decanted to yield as the residue the desired product the potassium salt of cyclohexanone oxime.

EXAMPLE 10

Preparation of N-(Cyclohexylideneaminooxymethyl)-2,6diethyl-3-methoxy-α-chloroacetanilide N-Chloromethyl-2,6-diethyl-3-methoxy-α-chloroacetanilide (0.05 mole) dissolved in ethanol (150 ml) and the potassium salt of cyclohexanone oxime (0.05 mole) dissolved in ethanol (100 ml) are charged into a glass reaction vessel and stirred at room temperature for a period of about 1 hour. After this time the reaction mixture is filtered to remove the potassium chloride formed. The filtrate is then stripped of ethanol, and the residue is dissolved in ethyl acetate. The resulting solution is washed with water, is dried over anhydrous magnesium sulfate and filtered. The filtrate is then stripped of solvent to yield the desired product N-(cyclohexylideneaminooxymethyl)-2,6-diethyl-3-methoxy-α-chloroacetanilide as the residue.

EXAMPLE 11

Preparation of the Sodium Salt of Acetaldehyde Oxime

Acetaldehyde oxime (0.10 mole) dissolved in ethanol (50 ml) and a solution of sodium hydroxide (0.11 mole) in ethanol (40 ml) are charged into a glass reaction vessel and are stirred for a period of about 30 minutes. After this time the reaction mixture is stripped of solvent, and the residue is triturated in benzene. The benzene is then decanted to yield as the residue the desired product the sodium salt of acetaldehyde oxime.

EXAMPLE 12

Preparation of N-(Ethylideneaminooxymethyl)-2,6-diethyl-3,5-dichloro-α-chloroacetanilide N-Chloromethyl-2,6-diethyl-3,5-dichloro-α-chloroacetanilide (0.05 mole) dissolved in ethanol (150 ml) and the sodium salt of acetaldehyde oxime (0.05 mole) dissolved in ethanol (100 ml) are charged into a glass reaction vessel and stirred at room temperature for a period of about 1 hour. After this time the reaction mixture is filtered to remove the sodium chloride formed. The filtrate is then stripped of ethanol, and the residue is dissolved in ethyl acetate. The resulting solution is washed with water, is dried over anhydrous magnesium sulfate and filtered. The filtrate is then stripped of solvent to yield the desired product N-(ethylideneaminooxymethyl)-2,6-diethyl-3,5-dichloro-α-chloroacetanilide as the residue.

EXAMPLE 13

Preparation of the Sodium Salt of Formaldehyde Oxime

Formaldehyde oxime (0.10 mole) dissolved in ethanol (50 ml) and a solution of sodium hydroxide (0.11 mole) in ethanol (40 ml) are charged into a glass reaction vessel and are stirred for a period of about 30 minutes. After this time the reaction mixture is stripped of solvent, and the residue is triturated in benzene. The benzene is then decanted to yield as the residue the desired product the sodium salt of formaldehyde oxime.

EXAMPLE 14

Preparation of N-(Methylideneaminooxymethyl)-2,6-diethyl-3-cyano-αchloroacetanilide N-Chloromethyl-2,6-diethyl-3-cyano-α-chloroacetanilide (0.05 mole) dissolved in ethanol (150 ml) and the sodium salt of formaldehyde oxime (0.05 mole) dissolved in ethanol (100 ml) are charged into a glass reaction vessel and stirred at room temperature for a period of about 1 hour. After this time the reaction mixture is filtered to remove the sodium chloride formed. The filtrate is then stripped of ethanol, and the residue is dissolved in ethyl acetate. The resulting solution is washed with water, is dried over anhydrous magnesium sulfate and filtered. The filtrate is then stripped of solvent to yield the desired product N-(methylideneaminooxymethyl)-2,6-diethyl-3-cyano-α-chloroacetanilide as the residue.

EXAMPLE 15

Preparation of the Sodium Salt of Cycloheptanone Oxime

Cycloheptanone oxime (0.10 mole) dissolved in ethanol (50 ml) and a solution of sodium hydroxide (0.11 mole) in ethanol (40 ml) are charged into a glass reaction vessel and are stirred for a period of about 30 minutes. After this time the reaction mixture is stripped of solvent, and the residue is triturated in benzene. The benzene is then decanted to yield as the residue the desired product the sodium salt of cycloheptanone oxime.

EXAMPLE 16

Preparation of N-(Cycloheptylideneaminooxymethyl)-2,6-diethyl-3-methylthio-α-bromoacetanilide N-Chloromethyl-2,6-diethyl-3-methylthio-α-bromoacetanilide (0.05 mole) dissolved in ethanol (150 ml) and the sodium salt of cycloheptanone oxime (0.05 mole) dissolved in ethanol (100 ml) are charged into a glass reaction vessel and stirred at room temperature for a period of about 1 hour. After this time the reaction mixture is filtered to remove the sodium chloride formed. The filtrate is then stripped of ethanol, and the residue is dissolved in ethyl acetate. The resulting solution is washed with water, is dried over anhydrous magnesium sulfate and filtered. The filtrate is then stripped of solvent to yield the desired product N-(cycloheptylideneaminooxymethyl)-2,6-diethyl-3-methylthio-α-bromoacetanilide as the residue.

EXAMPLE 17

Preparation of the Sodium Salt of Hexanaldehyde Oxime

Hexanaldehyde oxime (0.10 mole) dissolved in ethanol (50 ml) and a solution of sodium hydroxide (0.11 mole) in ethanol (40 ml) are charged into a glass reaction vessel and are stirred for a period of about 30 minutes. After this time the reaction mixture is stripped of solvent, and the residue is triturated in benzene. The benzene is then decanted to yield as the residue the desired product the sodium salt of hexanaldehyde oxime.

EXAMPLE 18

Preparation of N-(Hexylideneaminooxymethyl)-2,6-diethyl-3-chloromethyl-α-chloroacetanilide N-Chloromethyl-2,6-diethyl-3-chloromethyl-α-chloroacetanilide (0.05 mole) dissolved in ethanol (150 ml) and the sodium salt of hexanaldehyde oxime (0.05 mole) dissolved in ethanol (100 ml) are charged into a glass reaction vessel and stirred at room temperature for a period of about 1 hour. After this time the reaction mixture is filtered to remove the sodium chloride formed. The filtrate is then stripped of ethanol, and the residue is dissolved in ethyl acetate. The resulting solution is washed with water, is dried over anhydrous magnesium sulfate and filtered. The filtrate is then stripped of solvent to yield the desired product N-(hexylideneaminooxymethyl)-2,6-diethyl-3-chloromethyl-α-chloroacetanilide as the residue.

EXAMPLE 19

Preparation of the Sodium Salt of Butanaldehyde Oxime

Butanaldehyde oxime (0.10 mole) dissolved in ethanol (50 ml) and a solution of sodium hydroxide (0.11 mole) in ethanol (40 ml) are charged into a glass reaction vessel and are stirred for a period of about 30 minutes. After this time the reaction mixture is stripped of solvent, and the residue is triturated in benzene. The benzene is then decanted to yield as the residue the desired product the sodium salt of butanaldehyde oxime.

EXAMPLE 20

Preparation of N-(Butylideneaminooxymethyl)-2,6-diethyl-3-methoxymethyl-α-chloroacetanilide N-Chloromethyl-2,6-diethyl-3-methoxymethyl-α-chloroacetanilide (0.05 mole) dissolved in ethanol (150 ml) and the sodium salt of butanaldehyde oxime (0.05 mole) dissolved in ethanol (100 ml) are charged into a glass reaction vessel and stirred at room temperature for a period of about 1 hour. After this time the reaction mixture is filtered to remove the sodium chloride formed. The filtrate is then stripped of ethanol, and the residue is dissolved in ethyl acetate. The resulting solution is washed with water, is dried over anhydrous magnesium sulfate and filtered. The filtrate is then stripped of solvent to yield the desired product N-(butylideneaminooxymethyl)-2,6-diethyl-3-methoxymethyl-α-chloroacetanilide as the residue.

EXAMPLE 21

Preparation of the Sodium Salt of 3-Pentanone Oxime

3-Pentanone oxime (0.10 mole) dissolved in ethanol (50 ml) and a solution of sodium hydroxide (0.11 mole) in ethanol (40 ml) are charged into a glass reaction vessel and are stirred for a period of about 30 minutes. After this time the reaction mixture is stripped of solvent, and the residue is triturated in benzene. The benzene is then decanted to yield as the residue the desired product the sodium salt of 3-pentanone oxime.

EXAMPLE 22

Preparation of N-(1-Ethylpropylideneaminooxymethyl)-2,6-diethyl-3-(β-methylthioethyl)-α-chloroacetanilide N-Chloromethyl-2,6-diethyl-3-(β-methylthioethyl)-α-chloroacetanilide (0.05 mole) dissolved in ethanol (150 ml) and the sodium salt of 3-pentanone oxime (0.05 mole) dissolved in ethanol (100 ml) are charged into a glass reaction vessel and stirred at room temperature for a period of about 1 hour. After this time the reaction mixture is filtered to remove the sodium chloride formed. The filtrate is then stripped of ethanol, and the residue is dissolved in ethyl acetate. The resulting solution is washed with water, is dried over anhydrous magnesium sulfate and filtered. The filtrate is then stripped of solvent to yield the desired product N-(1-ethylpropylideneaminooxymethyl)-2,6-diethyl-3-(β-methylthioethyl)-α-chloroacetanilide as the residue.

EXAMPLE 23

Preparation of N-(Cyclopentylideneaminooxymethyl)-2,3,6-trimethyl-α-chloroacetanilide N-Chloromethyl-2,3,6-trimethyl-α-chloroacetanilide (0.05 mole) dissolved in ethanol (150 ml) and the sodium salt of cyclopentanone oxime (0.05 mole) dissolved in ethanol (100 ml) are charged into a glass reaction vessel and stirred at room temperature for a period of about 1 hour. After this time the reaction mixture is filtered to remove the sodium chloride formed. The filtrate is then stripped of ethanol, and the residue is dissolved in ethyl acetate. The resulting solution is washed with water, is dried over anhydrous magnesium sulfate and filtered. The filtrate is then stripped of solvent to yield the desired product N-(cyclopentylideneaminooxymethyl)-2,3,6-trimethyl-α-chloroacetanilide as the residue.

Additional exemplary compounds within the scope of the present invention which can be prepared by the procedures detailed in the foregoing examples are N-(methylideneaminooxymethyl)-2,6-dimethyl-3-ethyl-α-chloroacetanilide, N-(ethylideneaminooxymethyl)-2-methyl-3,6-diethyl-α-chloroacetanilide, N-(propylideneaminooxymethyl)-2-methyl-6-propyl-α-chloroacetanilide, N-(butylideneaminooxymethyl)-2-methyl-6-hexyl-α-chloroacetanilide, N-(pentylideneaminooxymethyl)-2,6-diethyl-3-bromo-α-chloroacetanilide, N-(hexylideneaminooxymethyl)-2,6-diethyl-3-fluoro-α-chloroacetanilide, N-(isopropylideneaminooxymethyl)-2,6-diethyl-3-iodo-α-chloroacetanilide, N-(cyclopropylideneaminooxymethyl)-2,6-diethyl-3-ethylthio-α-chloroacetanilide, N-(cyclobutylideneaminooxymethyl)-2,6-diethyl-3-propylthio-α-chloroacetanilide, N-(cyclopentylideneaminooxymethyl)-2,6-diethyl-3-hexylthio-α-chloroacetanilide, N-(cyclohexylideneaminooxymethyl)-2,6-diethyl-3-ethoxy-α-chloroacetanilide, N-(cycloheptylideneaminooxymethyl)-2,6-diethyl3-butoxy-α-chloroacetanilide, N-(ethylideneaminooxymethyl)-2,6-diethyl-3-hexyloxy-α-chloroacetanilide, N-(cyclopentylideneaminooxymethyl)-2,6-diethyl-3-butyl-α-chloroacetanilide, N-(cyclopentylideneaminooxymethyl)-2,6-diethyl-3-hexyl-α-chloroacetanilide, N-(cyclopentylideneaminooxymethyl)-2,6-diethyl-3-bromomethyl-α-chloroacetanilide, N-(cyclopentylideneaminooxymethyl)-2,6-diethyl-3-trifluoromethyl-α-chloroacetanilide, N-(cyclopentylideneaminooxymethyl)-2,6-diethyl3-iodomethyl-α-chloroacetanilide, N-(cyclopentylideneaminooxymethyl)-2,6-diethyl-3-ethoxymethyl-α-chloroacetanilide, N-(cyclopentylideneaminooxymethyl)-2,6-diethyl-3-butoxymethyl-α-chloroacetanilide, N-(cyclopentylideneaminooxymethyl)-2,6-diethyl-3-hexyloxymethyl-α-chloroacetanilide, N-(cyclopentylideneaminooxymethyl)-2,6-diethyl-3-β-methoxyethyl-α-chloroacetanilide, N-(cyclopentylaminooxymethyl)-2,6-diethyl-3-γ-methoxypropyl-α-chloroacetanilide, N-(ethylideneaminooxymethyl)-2,6-diethyl-3-δ-ethoxybutyl-α-chloroacetanilide, N-(cyclopentylideneaminooxymethyl)-2,6-diethyl-3-γ-ethylthiopropyl-α-chloroacetanilide, N-(cyclopentylideneaminooxymethyl)-2,6-diethyl-3-δ-propylthiobutyl-α-chloroacetanilide, N-(cyclopentylideneaminooxymethyl)-2-methyl-6-ethyl-α-chloroacetanilide and the like.

For practical use as herbicides the compounds of this invention are generally incorporated into herbicidal compositions which comprise an inert carrier and a herbicidally toxic amount of such a compound. Such herbicidal compositions, which can also be called formulations, enable the active compound to be applied conveniently to the site of the weed infestation in any desired quantity. These compositions can be solids such as dusts, granules, or wettable powders; or they can be liquids such as solutions, aerosols, or emulsifiable concentrates.

For example, dusts can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of herbicides can be dispersed under super-atmospheric pressure as aerosols. However, preferred liquid herbicidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems an inverted emulsion (water in oil) can be prepared for direct application to weed infestations.

A typical herbicidal composition according to this invention is illustrated by the following example, in which the quantities are in parts by weight.

EXAMPLE 24

Preparation of a Dust

| Product of Example 4 | 10 |
|---|---|
| Powdered Talc | 90 |

The above ingredients are mixed in a mechanical grinder-blender and are ground until a homogeneous, free-flowing dust of the desired particle size is obtained. This dust is suitable for direct application to the site of the weed infestation.

The compounds of this invention can be applied as herbicides in any manner recognized by the art. One method for the control of weeds comprises contacting the locus of said weeds with a herbicidal composition comprising an inert carrier and as an essential active ingredient, in a quantity which is herbicidally toxic to said weeds, a compound of the present invention. The concentration of the new compounds of this invention in the herbicidal compositions will vary greatly with the type of formulation and the purpose for which it is designed, but generally the herbicidal compositions will comprise from about 0.05 to about 95 percent by weight of the active compounds of this invention. In a preferred embodiment of this invention, the herbicidal compositions will comprise from about 5 to about 75 percent by weight of the active compound. The compositions can also comprise such additional substances as other pesticides, such as insecticides, nematocides, fungicides, and the like; stabilizers, spreaders, deactivators, adhesives, stickers, fertilizers, activators, synergists, and the like.

The compounds of the present invention are also useful when combined with other herbicides and/or defoliants, dessicants, growth inhibitors, and the like in the herbicidal compositions heretofore described. These other materials can comprise from about 5% to about 95% of the active ingredients in the herbicidal compositions. Use of combinations of these other herbicides and/or defoliants, dessicants, etc. with the compounds of the present invention provide herbicidal compositions which are more effective in controlling weeds and often provide results unattainable with separate compositions of the individual herbicides. The other herbicides, defoliants, dessicants and plant growth inhibitors, with which the compounds of this invention can be used in the herbicidal compositions to control weeds, can include chlorophenoxy herbicides such as 2,4-D, 2,4,5-T, MCPA, MCPB, 4(2,4-DB), 2,4-DEB, 4-CPB, 4-CPA, 4-CPP, 2,4,5-TB, 2,4,5-TES, 3,4-DA, silvex and the like; carbamate herbicides such as IPC, CIPC, swep, barban, BCPC, CEPC, CPPC, and the like; thiocarbamate and dithiocarbamate herbicides such as CDEC, metham sodium, EPTC, diallate, PEBC, perbulate, vernolate and the like; substituted urea herbicides such as norea, siduron, dichloral urea, chloroxuron, cycluron, fenuron, monuron, monuron TCA, diuron, linuron, monolinuron, neburon, buturon, trimeturon and the like; symmetrical triazine herbicides such as simazine, chlorazine, atraone, desmetryne, norazine, ipazine, prometryn, atrazine, trietazine, simetone, prometone, propazine, ametryne and the like; chloroacetamide herbicides such as alpha-chloro-N,N-dimethylacetamide, CDEA, CDAA, alpha-chloro-N-isopropylacetamide, 2-chloro-N-isopropylacetanilide, 4-(chloroacetyl)morpholine, 1-(chloroacetyl)-piperidine and the like; chlorinated aliphatic acid herbicides such as TCA, dalapon, 2,3-dichloropropionic acid, 2,2,3-TPA and the like; chlorinated benzoic acid and phenylacetic acid herbicides such as 2,3,6-TBA, 2,3,5,6-TBA, dicamba, tricamba, amiben, fenac, PBA, 2-methoxy-3,6-dichlorophenylacetic acid, 3-methoxy-2,6-dichlorophenylacetic acid, 2-methoxy-3,5,6-trichlorophenylacetic acid, 2,4-dichloro-3-nitrobenzoic acid and the like; and such compounds as aminotriazole, maleic hydrazide, phenyl mercuric acetate, endothal, biuret, technical chlordane, dimethyl 2,3,5,6-tetrachloroterephthalate, diquat, erbon, DNC, DNBP, dichlobenil, DPA, diphenamid, dipropalin, trifluralin, solan, dicryl, merphos, DMPA, DSMA, MSMA, potassium azide, acrolein, benefin, bensulide, AMS, bromacil, 2-(3,4-dichlorophenyl)-4-methyl-1,2,4-oxadiazolidine-3,5-dione, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, pyrichlor, sesone, terbacil, terbutol, TCBA, brominil, CP-50144, H-176-1, H-732, M-2901, planavin, sodium tetraborate, calcium cyanamid, DEF, ethyl xanthogen disulfide, sindone, sindone B, propanil and the like. Such herbicides can also be used in the methods and compositions of this invention in the form of their salts, esters, amides, and other derivatives whenever applicable to the particular parent compounds.

Weeds are undesirable plants growing where they are not wanted, having no economic value, and interfering with the production of cultivated crops, with the growing of ornamental plants, or with the welfare of livestock. Many types of weeds are known, including annuals such as pigweed, lambsquarters, foxtail, crabgrass, wild mustard, field pennycress, ryegrass, goose grass, chickweed, wild oats, velvetleaf, purslane, barnyardgrass, smartweed, knotweed, cocklebur, wild buckwheat, kochia, medic, corn cockle, ragweed, sowthistle, coffeeweed, croton, cuphea, dodder, fumitory, groundsel, hemp nettle, knawel, spurge, spurry, emex, jungle rice, pondweed, dog fennel, carpetweed, morningglory, bedstraw, ducksalad, naiad, cheatgrass, fall panicum, jimsonweed, witchgrass, switchgrass, watergrass, teaweed, wild turnip and sprangletop; biennials such as wild carrot, matricaria, wild barley, campion, chamomile, burdock, mullein, roundleaved mallow, bull thistle, hounds-tongue, moth mullein and purple star thistle; or perennials such as white cockle, perennial ryegrass, quackgrass, Johnsongrass, Canada thistle, hedge bindweed, Bermuda grass, sheep sorrel, curly dock, nutgrass, field chickweed, dandelion, campanula, field bindweed, Russian knapweed, mesquite, toadflax, yarrow, aster, gromwell, horsetail, ironweed, sesbania, bulrush, cattail, winter-cress, horsenettle, nutsedge, milkweed and sicklepod.

Similarly, such weeds can be classified as broadleaf or grassy weeds. It is economically desirable to control the growth of such weeds without damaging beneficial plants or livestock.

The new compounds of this invention are particularly valuable for weed control because they are toxic to many species and groups of weeds while they are relatively nontoxic to many beneficial plants. The exact amount of compound required will depend on a variety of factors, including the hardiness of the particular weed species, weather, type of soil, method of application, the kind of beneficial plants in the same area and the like. Thus, while the application of up to only about one or two ounces of active compound per acre may be sufficient for good control of a light infestation of weeds growing under adverse conditions, the application of 10 pounds or more of an active compound per acre may be required for good control of a dense infestation of hardy perennial weeds growing under favorable conditions.

The herbicidal toxicity of the new compounds of this invention can be illustrated by many of the established testing techniques known to the art, such as pre- and post-emergence testing.

The herbicidal activity of the compounds of this invention was demonstrated by experiments carried out for the pre-emergence control of a variety of weeds. In these experiments small plastic greenhouse pots filled with dry soil were seeded with the various weed seeds. Twenty-four hours or less after seeding the pots were sprayed with water until the soil was wet and the test compound formulated as an aqueous emulsion of an acetone solution containing emulsifiers was sprayed at the indicated concentrations on the surface of the soil.

After spraying, the soil containers were placed in the greenhouse and provided with supplementary heat as required and daily or more frequent watering. The plants were maintained under these conditions for a period of 21 days, at which time the condition of the plants and the degree of injury to the plants was rated on a scale of from 0 to 10, as follows: 0 = no injury, 1,2 = slight injury, 3,4 = moderate injury, 5,6 = moderately severe injury, 7,8,9 = severe injury and 10 = death. The effectiveness of these compounds is demonstrated by the data in Table I.

TABLE I

| Weed Species | INJURY RATING Product of Example 4 (lbs./acre) | | | | |
|---|---|---|---|---|---|
| | 8 | 4 | 2 | 1 | .5 |
| Yellow Nutsedge | 10 | 10 | 10 | 10 | 0 |
| Wild Oats | 10 | 10 | 5 | 4 | 0 |
| Johnsongrass | 10 | 10 | 10 | 9 | 4 |
| Pigweed | 10 | 10 | 10 | 8 | 7 |
| Wild Mustard | 10 | 8 | 0 | 10 | 10 |
| Yellow Foxtail | 10 | 10 | 10 | 10 | 10 |
| Barnyardgrass | 10 | 10 | 10 | 10 | 8 |
| Crabgrass | 10 | 10 | 10 | 10 | 10 |
| Cheatgrass | 10 | 10 | 10 | 10 | 10 |
| Jimsonweed | 10 | 5 | — | — | — |
| Velvetleaf | 5 | 3 | — | — | — |
| Morningglory | 7 | 5 | — | — | — |

The herbicidal activity of the compounds of this invention can also be illustrated by experiments carried out for the post-emergence control of a variety of weeds. In these experiments the compounds to be tested are formulated as aqueous emulsions and sprayed at the indicated dosage on the foliage of the weeds that have attained a prescribed size. After spraying, the plants are placed in a greenhouse and watered daily or more frequently. Water is not applied to the foliage of the treated plants. The severity of the injury is determined 10 to 15 days after treatment and is rated on the scale of from 0 to 10 heretofore described.

We claim:
1. A compound of the formula

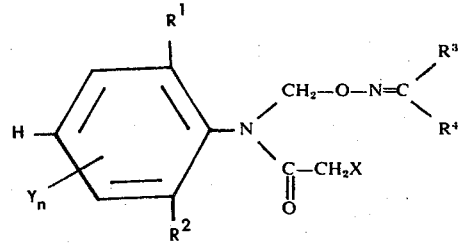

wherein $R^1$ and $R^2$ are each alkyl; Y is selected from the group consisting of hydrogen, alkyl, alkoxy, halogen, cyano, alkylthio, haloalkyl, alkoxyalkyl and alkylthioalkyl; $n$ is an integer from 0 to 2; $R^3$ and $R^4$ are each selected from the group consisting of hydrogen and alkyl, or $R^3$ and $R^4$ together can form a cycloalkyl group of from 3 to 7 carbon atoms; and X is chlorine or bromine.

2. The compound of claim 1, N-(cyclopentylideneaminooxymethyl)-2,6-diethyl-α-chloroacetanilide.

3. The compound of claim 1, N-(cyclobutylideneaminooxymethyl)-2,6-dimethyl-α-chloroacetanilide.

4. The compound of claim 1, N-(1-methylpropylideneaminooxymethyl)-2,6-dipropyl-α-chloroacetanilide.

5. The compound of claim 1, N-(cyclohexylideneaminooxymethyl)-2,6-diethyl-3-methoxy-α-chloroacetanilide.

6. The compound of claim 1, N-(ethylideneaminooxymethyl)-2,6-diethyl-3,5-dichloro-α-chloroacetanilide.

7. The compound of claim 1, N-(methylideneaminooxymethyl)-2,6-diethyl-3-cyano-α-chloroacetanilide.

8. The compound of claim 1, N-(cyclopentylideneaminooxymethyl)-2-methyl-6-ethyl-α-chloroacetanilide.

9. A herbicidal composition comprising an inert carrier and, as an essential active ingredient, in a quantity toxic to weeds, a compound of claim 1.

10. A method of controlling weeds which comprises contacting said weeds with a herbicidal composition comprising an inert carrier and, as an essential active ingredient, in a quantity toxic to weeds, a compound of claim 1.

* * * * *